(12) United States Patent
Kwan et al.

(10) Patent No.: US 9,476,858 B2
(45) Date of Patent: Oct. 25, 2016

(54) CLAMP-ON-TYPE ULTRASONIC CONCENTRATION METERING SYSTEM AND METHOD

(71) Applicant: WESS GLOBAL, INC., Chungcheongnam-do (KR)

(72) Inventors: Nam Won Kwan, Chungcheongnam-do (KR); In Soo Kim, Chungcheongnam-do (KR); Jin Woo Kim, Chungcheongnam-do (KR); Jong Seop Park, Chungcheongnam-do (KR)

(73) Assignee: WESS GLOBAL, INC., Cheonan-si, Chungcheongnam-do (KR)

( * ) Notice: Subject to any disclaimer, the term of this patent is extended or adjusted under 35 U.S.C. 154(b) by 260 days.

(21) Appl. No.: 14/349,799

(22) PCT Filed: Sep. 20, 2012

(86) PCT No.: PCT/KR2012/007532
§ 371 (c)(1),
(2) Date: Apr. 4, 2014

(87) PCT Pub. No.: WO2013/051800
PCT Pub. Date: Apr. 11, 2013

(65) Prior Publication Data
US 2014/0238115 A1    Aug. 28, 2014

(30) Foreign Application Priority Data
Oct. 6, 2011   (KR) .......................... 10-2011-0101567

(51) Int. Cl.
*G01N 29/02* (2006.01)
*G01N 29/024* (2006.01)
(Continued)

(52) U.S. Cl.
CPC ............ *G01N 29/02* (2013.01); *G01N 29/024* (2013.01); *G01N 29/032* (2013.01); *G01N 29/222* (2013.01); *G01N 2291/02818* (2013.01); *G01N 2291/02836* (2013.01); *G01N 2291/048* (2013.01); *G01N 2291/2634* (2013.01)

(58) Field of Classification Search
USPC ....................................................... 73/61.79
See application file for complete search history.

(56) References Cited

U.S. PATENT DOCUMENTS

| | | | | |
|---|---|---|---|---|
| 4,095,457 A | * | 6/1978 | Koda | .................... G01F 1/667 |
| | | | | 374/117 |
| 4,220,040 A | * | 9/1980 | Noguchi | .............. G01N 29/024 |
| | | | | 435/807 |
| 4,628,725 A | * | 12/1986 | Gouilloud | ............ E21B 47/101 |
| | | | | 367/31 |

(Continued)

FOREIGN PATENT DOCUMENTS

| | | |
|---|---|---|
| JP | 06-027695 B2 | 4/1994 |
| JP | 06-094688 A | 4/1994 |

(Continued)

*Primary Examiner* — Hezron E Williams
*Assistant Examiner* — Mark A Shabman
(74) *Attorney, Agent, or Firm* — Rabin & Berdo, P.C.

(57) ABSTRACT

Disclosed is a clamp-on-type ultrasonic concentration metering system and method. The clamp-on-type ultrasonic concentration metering system includes an ultrasonic sensor portion and a concentration meter. The ultrasonic sensor portion is attached to an outer wall of a pipe through which a fluid to be measured flows and that transmits and receives an ultrasonic signal through a wall of the pipe. The concentration meter measures a concentration of a substance according an intensity of the ultrasonic signal that is received after passing through the wall of the pipe, the fluid to be measured, and the wall of the pipe by means of the ultrasonic sensor portion.

10 Claims, 11 Drawing Sheets

(a) ATTACHED TO OUTER WALL (b) STATE INSIDE PIPE

(51) Int. Cl.
 *G01N 29/032* (2006.01)
 *G01N 29/22* (2006.01)

(56) References Cited

U.S. PATENT DOCUMENTS

| | | | |
|---|---|---|---|
| 5,121,629 A | 6/1992 | Alba | |
| 5,473,934 A * | 12/1995 | Cobb | G01N 29/024 73/597 |
| 2010/0095782 A1 * | 4/2010 | Ferencz | G01F 1/66 73/861.28 |
| 2011/0271769 A1 * | 11/2011 | Kippersund | G01F 1/42 73/861.28 |

FOREIGN PATENT DOCUMENTS

| | | |
|---|---|---|
| JP | 2003-501254 A | 1/2003 |
| JP | 2008-164362 A | 7/2008 |

\* cited by examiner (a) RT MODE    (b) PM MEASUREMENT MODE (a) RT MODE   (b) PM MEASUREMENT MODE

CLAMP-ON-TYPE ULTRASONIC CONCENTRATION METERING SYSTEM AND METHOD

TECHNICAL FIELD

The present invention relates to a clamp-on-type ultrasonic concentration metering system and method, and more particularly to a clamp-on-type ultrasonic concentration metering system and method for which an ultrasonic sensor portion is attached to an outer wall of a pipe and which can perform reliable concentration measurement according to process operation states and changes in a fluid circulation environment by using a concentration meter equipped with a Process Condition Monitoring (PCM) function.

BACKGROUND ART

Generally, an ultrasonic concentration meter is a measuring instrument which measures the concentration of various kinds of suspended solids, in real time, either which flow along with a fluid through a pipe or which settles in many types of waterworks plants, such as a water purification plant, a water treatment plant, or a sewage treatment plant.

FIG. 1 is a diagram illustrating the structure of an ultrasonic concentration meter inserted in a pipe according to a conventional art.

As illustrated in FIG. 1, a conventional ultrasonic concentration meter 10 is configured such that an ultrasonic sensor for measuring a concentration is inserted in a pipe 1, an ultrasonic signal radiated from an ultrasonic transmission sensor 11 attenuates by being scattered or absorbed by impurities, foreign substances, suspended solids, etc. contained in a fluid (sample solution) while passing through the fluid, and then reaches an ultrasonic reception sensor 12, and a concentration of a substance in the fluid is measured according to the intensity of the received ultrasonic signal.

The conventional ultrasonic concentration meter 10 has a problem that, when removing the ultrasonic transmission sensor 11 and the ultrasonic reception sensor 12 from the ultrasonic concentration meter 10 for the purpose of maintenance (i.e. replacement or cleaning), the stream of the fluid is adjusted to bypass the ultrasonic concentration meter 10 by closing valves installed at an inlet and an outlet of the ultrasonic concentration meter 10, respectively and opening a bypass valve, and then replacement of the sensors can be carried out thereafter.

Accordingly, the conventional ultrasonic concentration meter 10 needs to be additionally equipped with a bypass pipeline and a bypass valve, which increases installation cost and imposes a limitation on the size of an installation space.

Furthermore, since the entire surfaces of the ultrasonic transmission sensor 11 and the ultrasonic reception sensor 12 are constantly in contact with the fluid which is flowing through the inside of the ultrasonic concentration meter, sludge is likely to stick to the surfaces of the ultrasonic transmission sensor 11 and the ultrasonic reception sensor 12 depending on kinds and characteristics of the suspended solids contained in the fluid when the fluid is maintained at a low velocity for a long period of time or when the concentration of the suspended solids in the fluid is high, attenuating the sensitivity of the sensors. For this reason, the conventional ultrasonic concentration meter has a problem that the sensors need to be periodically cleaned.

That is, since the fluid, a measurement subject, contains various kinds of pollutants and suspended solids which are targets for concentration measurement, the likelihood that the ultrasonic transmission sensor 11 and the ultrasonic reception sensor 12 are broken down is likely to increase.

DISCLOSURE

Technical Problem

Accordingly, the present invention has been made keeping in mind the above problems occurring in the prior art, and an object of the present invention is to provide a clamp-on-type ultrasonic concentration metering system and an ultrasonic concentration metering method which have the following advantages: a high sensitivity ultrasonic sensor is attached to an outer wall of a pipe so that the ultrasonic sensor is free from malfunctioning attributable to sludge sticking to the ultrasonic sensor; the ultrasonic sensor is protected from sludge so that it can be used for a long period of time without concerns of malfunctioning; and it is not necessary to have a bypass pipe for maintenance of the ultrasonic sensor so that design cost is reduced and that maintenance can be performed without suspending an ongoing process.

Another object of the present invention is to provide a clamp-on-type ultrasonic concentration metering system and an ultrasonic concentration metering method which adopt a PCM algorithm, which can monitor process operation conditions and changes in a circulation environment and which controls peripheral devices according to the process operation conditions in a pipe, thereby enabling an automatic operation control and maximizing process operation efficiency.

Technical Solution

In order to accomplish the above object(s), according to one aspect, there is provided a clamp-on-type ultrasonic concentration metering system including: an ultrasonic sensor portion that is attached to an outer wall of a pipe through which a fluid to be measured flows and that transmits and receives an ultrasonic signal through an wall of the pipe; and a concentration meter that measures a concentration of a substance according an intensity of the ultrasonic signal that is received after passing through the wall of the pipe, the fluid to be measured, and the wall of the pipe by means of the ultrasonic sensor portion.

The ultrasonic sensor portion includes: an ultrasonic transmission sensor that is attached to one-side wall of the pipe and transmits an ultrasonic signal which can pass through the fluid; and an ultrasonic reception sensor that is attached to the opposite-side wall of the pipe and receives the ultrasonic signal transmitted by the ultrasonic transmission sensor.

Each of the ultrasonic transmission sensor and the ultrasonic reception sensor includes: a piezoelectric element that transmits or receives an ultrasonic signal; a sound-absorbing member that reduces residual vibrations of the ultrasonic transmission sensor or the ultrasonic reception sensor; an acoustic window that protects the piezoelectric element and maximizes ultrasonic signal transmission characteristics transmitted between media through impedance matching with the fluid to be measured; an external housing having a protective, waterproof, and noise-shielding structure that can protect the ultrasonic transmission sensor or the ultrasonic reception sensor from surrounding environments; and a connecter electrically to the concentration meter.

Each of the ultrasonic transmission sensor and the ultrasonic reception sensor includes a sensor that accommodates the corresponding sensor and an external casing that accommodates the sensor holder and is attached to the pipe.

The external casing is any one type selected from the group consisting of a handcuff type which fixedly installs the sensor, a clamp type by which fixedly installs the sensor, and a saddle type which movably installs the sensor.

The external casing uses a casing guide which aligns the external casing with respect to the pipe when the external casing is designed originally.

The sensor holder is pivotably supported to the external casing, and the sensor is rotatable, so that an angle of the sensor with respect to the pipe is adjustable according to the shape of a radiating surface of the sensor.

The concentration meter includes: an operation switch which is operated for process operation, setting of menu, and outputting of measurements during concentration measurement; a sensor transception portion that amplifies an ultrasonic signal transmitted or received by the ultrasonic sensor portion to enable high power transmission and high gain reception of the ultrasonic signal; a control portion mounted with a Process Condition Monitoring (PCM) algorithm, which performs an optimum concentration measurement mode for a field, determines whether a process operation state is normal or abnormal, and performs operation and control related to concentration measurement; a power supply portion that supplies power needed by the control portion and the sensor transception portion; and an external output portion that outputs measurements of concentration measured by the control portion.

The external output portion is connected to a display means and provides a numeric display function, a process display function, a diagnosis display function, and a data trend display function.

The PCM algorithm comprises a subsonic filter that measures a sound velocity of the fluid to be measured and determines a change in the sound velocity, a temperature sensor that measures a temperature of the fluid to be measured and determines a change in the temperature, and a signal filter that receives the ultrasonic signal and determines an intensity of the ultrasonic signal and an amount of change in the intensity of the ultrasonic signal.

The PCM algorithm checks a process state using the subsonic filter, the process state and a pipe filling state using the temperature filter, and a dispersion uniformity of suspended solids that are targets of concentration measurement using the signal filter, determines a process operation state by collating results from each filter, determines the dispersion uniformity of the suspended solids, and provides a process operator with information about measurements of effective suspended solids, the process operation state, and the pipe filling state during operation of a process.

The PCM algorithm mode has measurement modes including a real time mode in which a change in concentration is monitored in real time according to an on-site operation pattern and a process monitoring mode in which a change in concentration is automatically measured only while a process is running, based on a result of a process condition monitoring (PCM).

A clamp-on-type ultrasonic concentration metering method that is performed by using a concentration meter, which measures a concentration of a substance according to an intensity of an ultrasonic signal by means of an ultrasonic sensor portion that is installed outside a pipe, through which a fluid to be measured flows, and that transmits and receives the ultrasonic signal, the method including: a Real Time (RT) mode step of measuring a concentration change in real time by using the ultrasonic sensor portion and the concentration meter according to on-site operation patterns; and a Process Monitoring (PM) mode step of automatically measuring a concentration change by using the ultrasonic sensor portion and the concentration meter, based on a result of a Process Condition Monitoring (PCM) only while a process is running.

The PM mode step includes: a step of measuring a temperature and a sound velocity of the fluid to be measured and measuring a dispersion uniformity (EEA) of Suspended Sludge (SS) that is a target of concentration measurement; a step of verifying measurements, which are being presently measured, by filtering the ultrasonic signal received by the ultrasonic sensor portion and a temperature signal, and measuring a temperature, a sound velocity, and an EEA value when the measurements are verified to be invalid; a step of diagnosing a state as "empty" for a pipe filling state and as "stop" for a process operation state when the presently measured sound velocity exceeds a reference sound velocity and the presently measured temperature is above a first reference temperature; a step of diagnosing a state as "full" for the pipe filling state and "stop" for the process operation state when the presently measured sound velocity exceeds the reference sound velocity and the presently measured temperature is the first reference temperature or below; a step of counting up a process operation state diagnosis count when the presently measured sound velocity is equal to or lower than the reference sound velocity and the presently measured temperature is the first reference temperature or below; a step of maintaining past effective measurements when the process operation state diagnosis count is equal to or larger than a reference count and maintaining past measurements when the process operation state diagnosis count is smaller than the reference count and the presently measured temperature is above a second reference temperature; a step of diagnosing a state as "full" for the pipe filling state and "run" for the process operation state when the process operation state diagnosis count is smaller than the reference count, the presently measured temperature is the second reference temperature or below, and a PM state variable is not "0"; and a step of resetting the measured EEA value, maintaining effective past measurements when a difference (d(EEA)) between the measured EEA values is less than a reference EEA value, and stopping the PM mode step when the d(EEA) is equal to or greater than the reference EEA value.

Advantageous Effects

The clamp-on-type ultrasonic concentration metering system and method according to one embodiment of the present invention has the following advantages: an ultrasonic sensor portion attached to an outer wall of a pipe is used to measure a flow rate using a time difference between an ultrasonic transmission sensor and an ultrasonic reception sensor; the sensors are protected from sludge so that the sensors can be used for a long period of time without concerns of malfunctioning; and it is not necessary to have a bypass pipe for maintenance of the sensors so that design cost is reduced and that maintenance can be performed without suspending an ongoing process.

According to the present invention, the ultrasonic transmission sensor and the ultrasonic reception sensor enable easy on-site installation and shifting, are stably situated when they are installed, are immune from external noise, have a structurally flexible design to allow expansion of functions, which maximizes convenience of users, and can perform reliable measurement immune from vibrations of peripheral pipes.

In addition, according to the present invention, since the PCM algorithm which can control peripheral devices according to process operation conditions inside a pipe, thereby enabling automatic control on a process and maximizing process operation efficiency, is adopted, automatic control on concentration measurement according to an on-site operation pattern becomes possible. The automatic control reduces an amount of sludge, which leads to energy saving attributable to reduction in use of a pump for sludge treatment. Moreover, it is possible to precisely and accurately measure a concentration of sludge during treatment, thereby preventing excessive chemical treatment on sludge.

In addition, according to the present invention, it is possible to precisely and accurately measure a total amount of pollutants through concentration measurement of the pollutants, thereby enabling construction of a management system which reflects actual toxicity or harmfulness of the pollutants in a treatment process.

DESCRIPTION OF THE REFERENCE NUMERALS IN THE DRAWINGS

Figure 1:
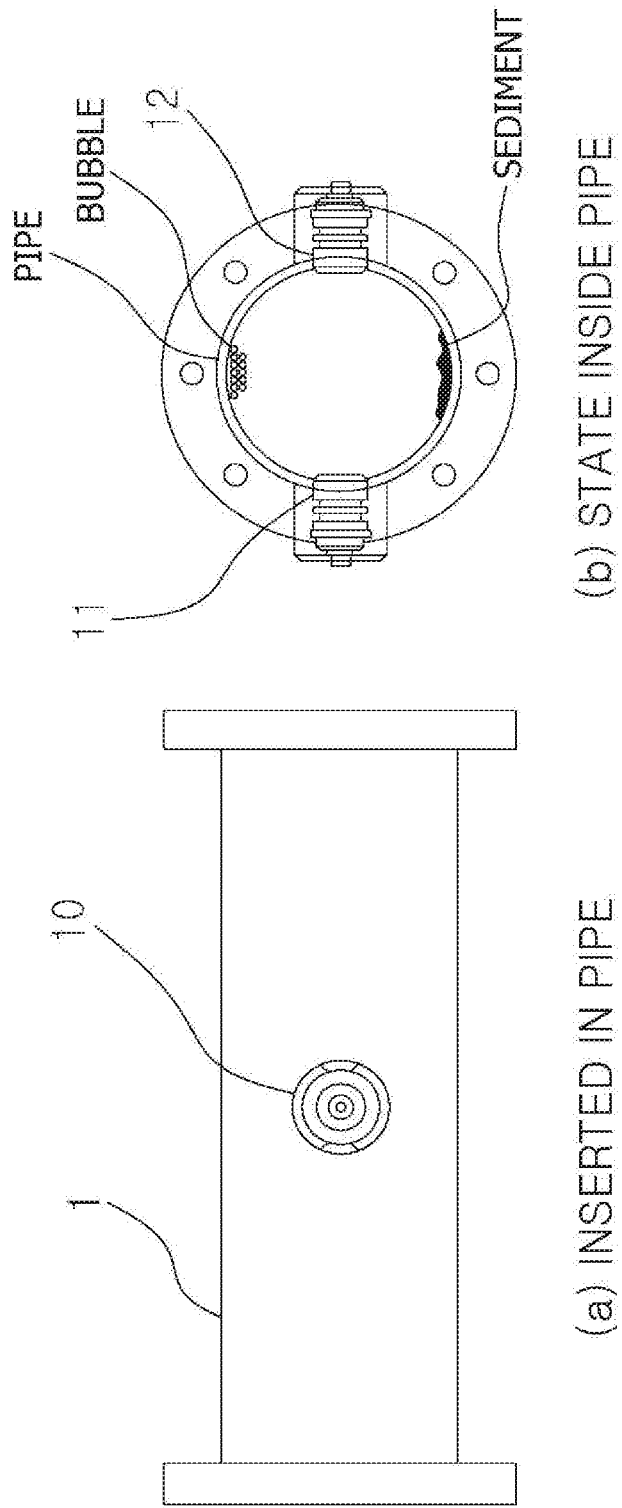
FIG. 1 is a diagram illustrating the structure of an ultrasonic concentration meter inserted in a pipe according to a conventional art.
Figure 2:
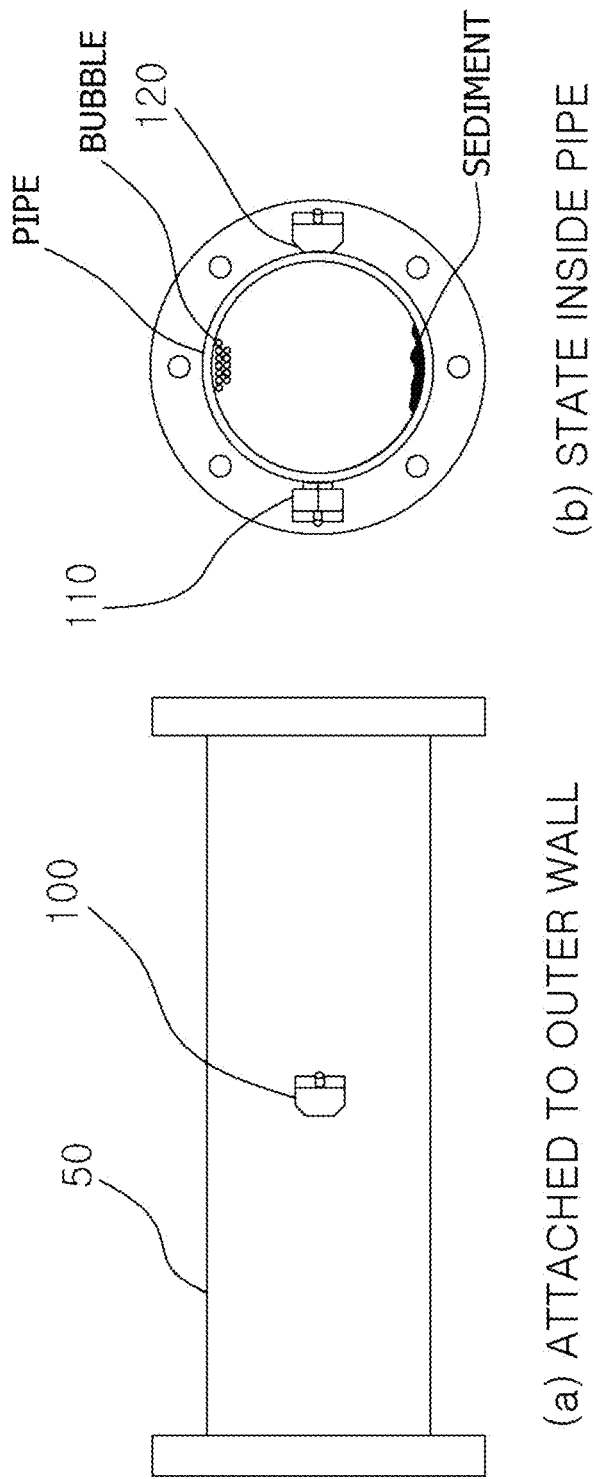
FIG. 2 is a diagram illustrating an installed state of a clamp-on-type ultrasonic concentration metering system according to one embodiment of the present invention.
Figure 3:
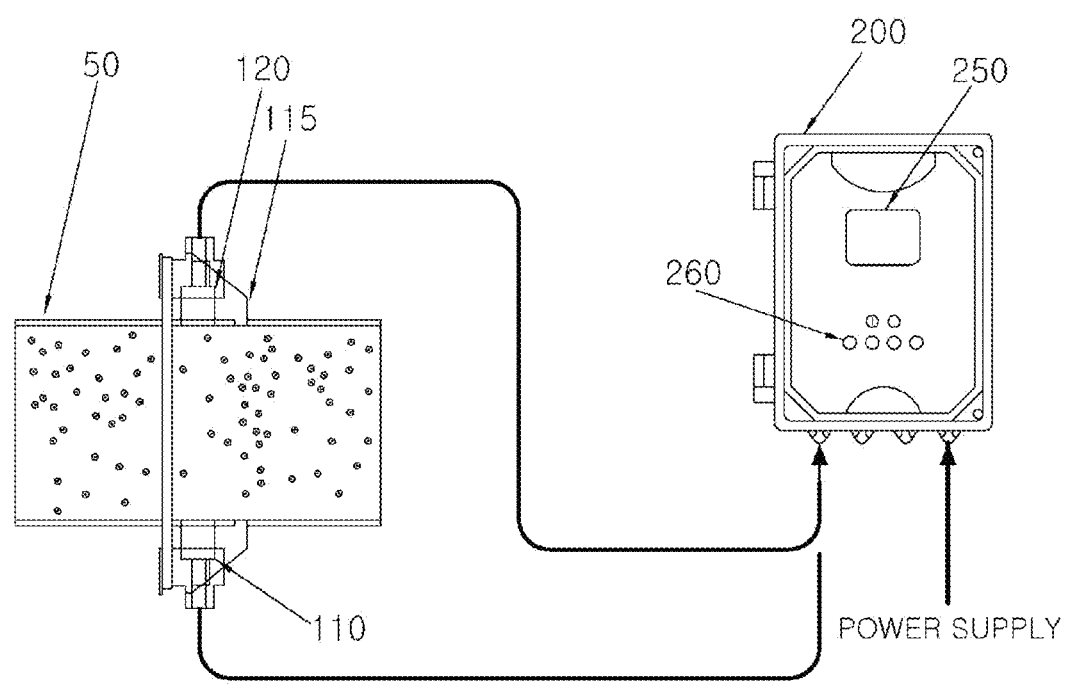
FIG. 3 is a diagram illustrating an outline of the clamp-on-type ultrasonic concentration metering system according to one embodiment of the present invention.
Figure 4:
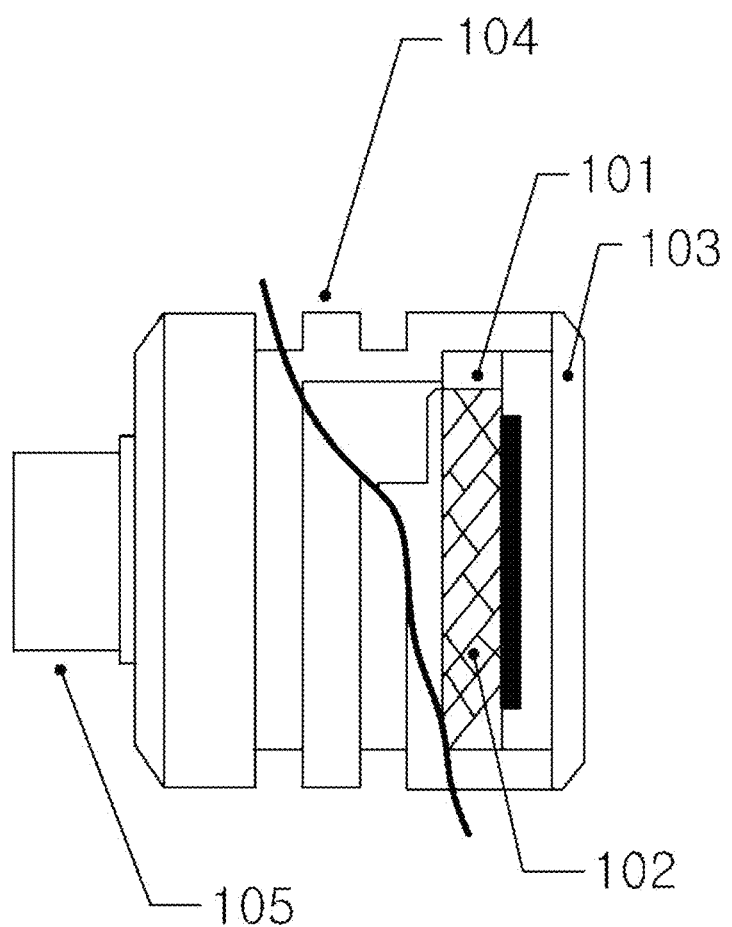
FIG. 4 is a diagram illustrating an interior structure of an ultrasonic sensor portion according to one embodiment of the present invention.

50: Pipe
100: Ultrasonic sensor portion
101: Piezoelectric element
102: Sound-absorbing member
103: Acoustic window
104: External housing
105: Connector
106: Sensor holder
107: External casing
108: Casing guide
110: Ultrasonic transmission sensor
115: Sensor-mounted kit
120: Ultrasonic reception sensor
200: Concentration meter
210: Sensor transception portion
220: Control portion
25: Data storage portion
230: Power supply portion
240: External output portion
250: Display means
310: Subsonic filter
320: Temperature filter
330: Signal filter

MODE FOR INVENTION

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims. Throughout the drawings, the same reference numerals will refer to the same or like parts.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, exemplary embodiments of the present invention will be described in detail with reference to the accompanying drawings.

With reference to FIGS. 2 to 11, a clamp-on-type ultrasonic concentration metering system according to one embodiment of the present invention includes, but is not limited to, an ultrasonic sensor portion 100 and a concentration meter 200. The ultrasonic sensor portion 100 is attached to an outer wall of a pipe 50 through which a fluid serving as a subject of measurement flows, and transmits and receives an ultrasonic signal through the wall of the pipe 50. The concentration meter 200 measures a concentration of a substance in the fluid according to the intensity of the ultrasonic signal which is transmitted to sequentially pass through the wall of the pipe 50, the fluid which is a subject of measurement, and the wall of the pipe 50 by means the ultrasonic sensor portion 100.

The ultrasonic sensor portion 100 is composed of an ultrasonic transmission sensor 110 which is installed on a portion of the outer wall of the pipe 50 and transmits an ultrasonic signal that can pass through the fluid; and an ultrasonic reception sensor 120 which is installed on the opposite wall of the pipe 50 and receives the ultrasonic signal that passed through the fluid after being transmitted from the ultrasonic transmission sensor 110.

In this case, the ultrasonic transmission sensor 110 and the ultrasonic reception sensor 120 are stably mounted in a sensor-mounted kit 115.

The ultrasonic transmission sensor 110 and the ultrasonic reception sensor 120 each include a piezoelectric element 101, a sound-absorbing member 102, an acoustic window 103, an external housing 104, and a connector 105. The piezoelectric element 101 is a key element of a sensor and is a main factor that determines sensitivity. The sound-absorbing member 102 affects ringing characteristics, a use frequency band, and the sensitivity of a sensor. The acoustic window 103 protects the piezoelectric element 101 and maximizes ultrasonic transmission characteristics between media (i.e. between a sensor and a pipe) through impedance matching with the fluid which is a subject of measurement. The external housing 104 protects the sensors 110 and 120 from the environment and has a waterproof and noise-shielding structure. The connector 105 is electrically connected to the concentration meter 200.

In particular, the acoustic window 103 is a factor that affects acoustic matching and determines operation efficiency. Accordingly, the acoustic window 103 should be selected in consideration of corrosion resistance, transmission efficiency, etc. Preferably, the connector 105 is designed to have a waterproof structure.

As described above, the ultrasonic transmission sensor 110 and the ultrasonic reception sensor 120 are highly dependent on sensitivity, compared to an insertion-type sensor. Accordingly, there is a demand for development of a high sensitivity piezoelectric element or a high performance sensor transception portion 210.

Figure 5:
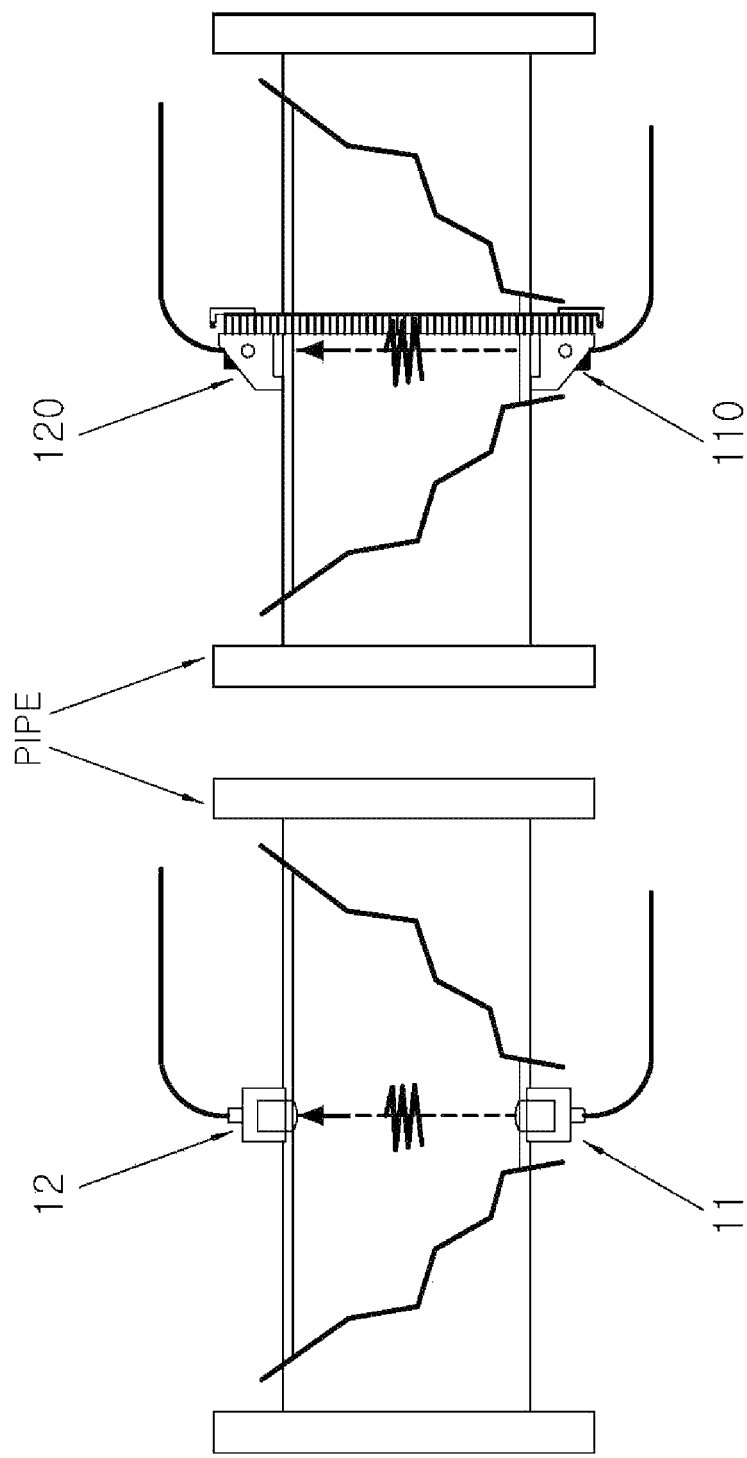
FIG. 5 is a diagram illustrating a signal transmission path of the ultrasonic sensor portion according to one embodiment of the present invention.

That is, as illustrated in FIG. 5, a general ultrasonic sensor measures a physical quantity in the air or under water by mainly using a PZT piezoelectric element. As to the ultrasonic transmission sensor 110 and the ultrasonic reception sensor 120 of the clamp-on-type puller, since the ultrasonic waves are transmitted, along a transmission path (i.e. the pipe 50→the fluid as a subject of measurement→the pipe 50), up to the ultrasonic reception sensor 120, various materials can be used to form the transmission path. Signal attenuation severely occurs while a signal passes through the transmission path. Accordingly, development of a high sensitivity piezoelectric element and a high performance sensor transception portion 210 is needed to ensure reliable measurement.

A coupling structure for attaching the ultrasonic transmission sensor 110 and the ultrasonic reception sensor 120 should be stably installed on the pipe 50 to secure high reliability of measurement. Furthermore, the ultrasonic transmission sensor 110 and the ultrasonic reception sensor 120 need to be easily installed and shifted after being installed, In addition, noise must not be transmitted to the sensors, and the installed structure must be stably situated.

In order to meet these needs for the coupling structure of the sensors 110 and 120, the coupling structure may be a handcuff type which facilitates installation and fixation of the sensors and fixedly installs the sensors, a saddle type which assures high reliability in installation and fixation and fixedly installs the sensors, and a clamp type which facilitates installation, assures high reliability in installation and fixation, and movably installs the sensors.

Figure 7:
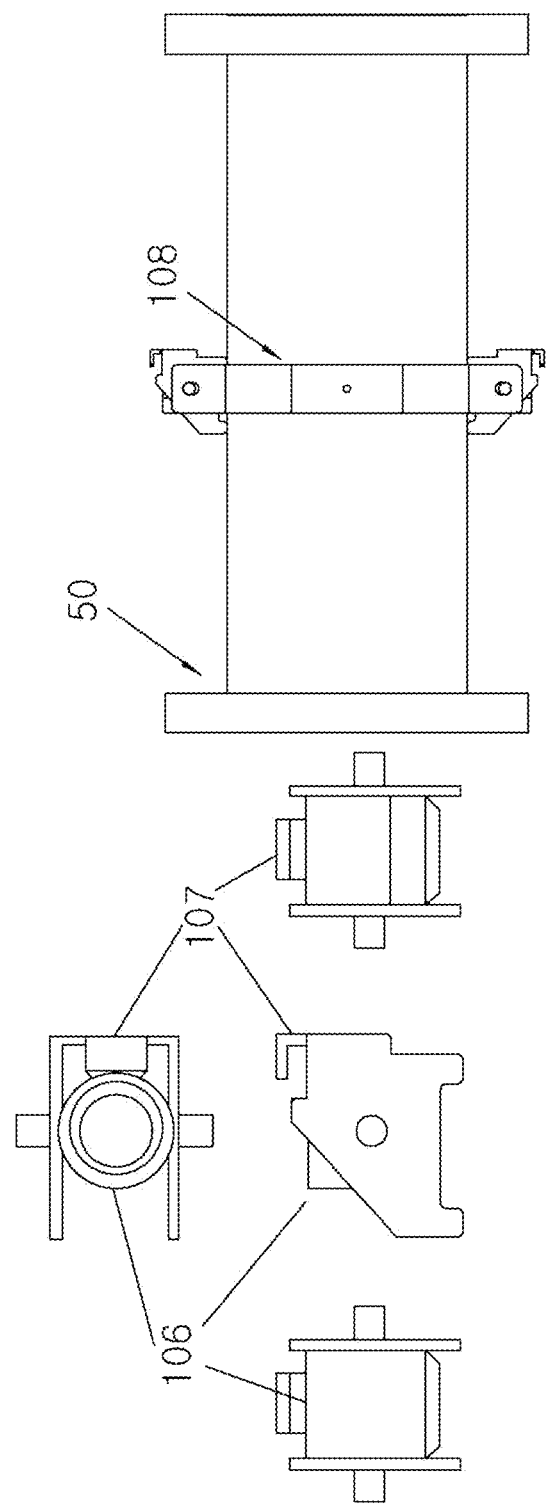
FIG. 7 is a diagram illustrating the structure of the ultrasonic sensor portion according to one embodiment of the present invention.

The saddle-type coupling structure, as illustrated in FIG. 7, includes a sensor holder 106 which accommodates the sensors therein, an external casing 107 which accommodates the sensor holder 106 and is installed on the pipe 50, and a casing guide 108 which is used to align the external casing 107 when the external casing 107 is designed originally.

The sensor holder 106 and the external casing 107 are made from stainless steel to prevent corrosion, which commonly occurs in water treatment plants; and to prevent pollution and corrosion attributable to corrosive gases and wastewater. The sensor holder 106 and the external casing 107 are designed to be lightweight so that convenience for storage and transportation thereof can be maximized.

For the purpose of smooth contact between the sensors 110 and 120 and the pipe 50, the external casing 107 and the sensor holder 106 are connected in a pivotable manner. In addition, the connection is made in consideration of smoothness of the pipe and expansion of functions after installation so that other equipment can be additionally connected. The sensor holder 106 is structured to be rotatable so that an angle of the sensor holder 106 with respect to the pipe can be automatically adjusted according to the shapes of radiating surfaces of the inserted sensors 110 and 120. Accordingly, convenience for installation can be maximized.

Figure 6:
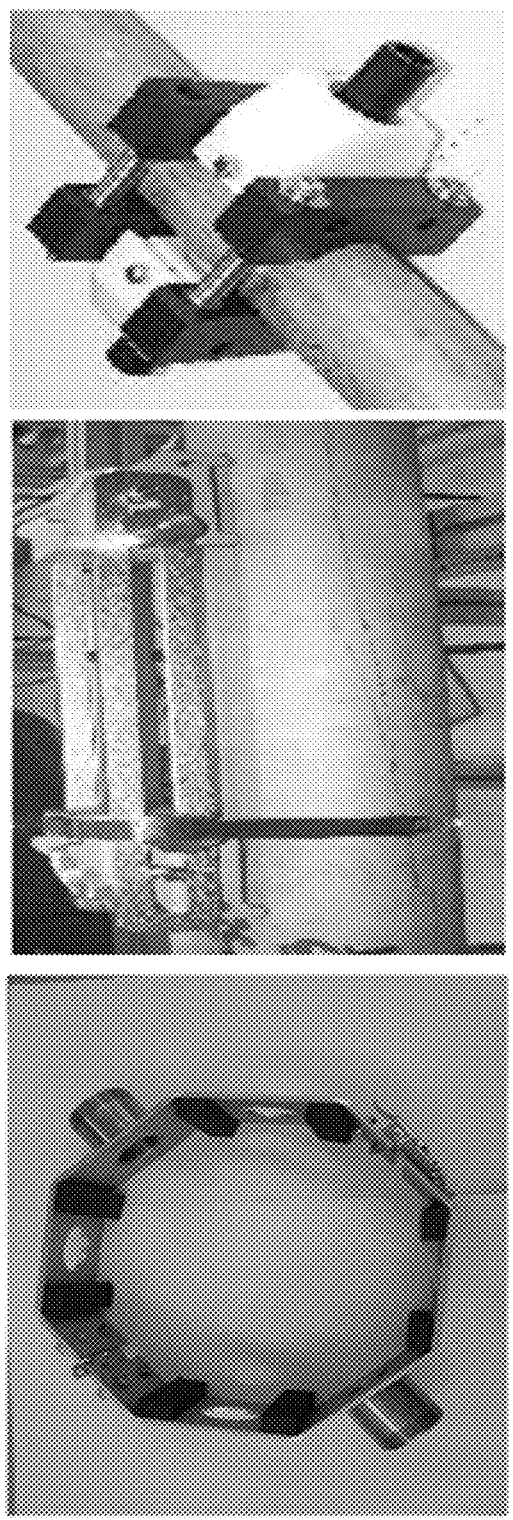
FIG. 6 is a diagram illustrating various forms of external casings according to one embodiment of the present invention.

In addition, as illustrated in FIG. 6, the external casing 107 may be any one type which is selected from among the handcuff type, the clamp type, and the saddle type according to the coupling structure of the sensors.

Figure 8:
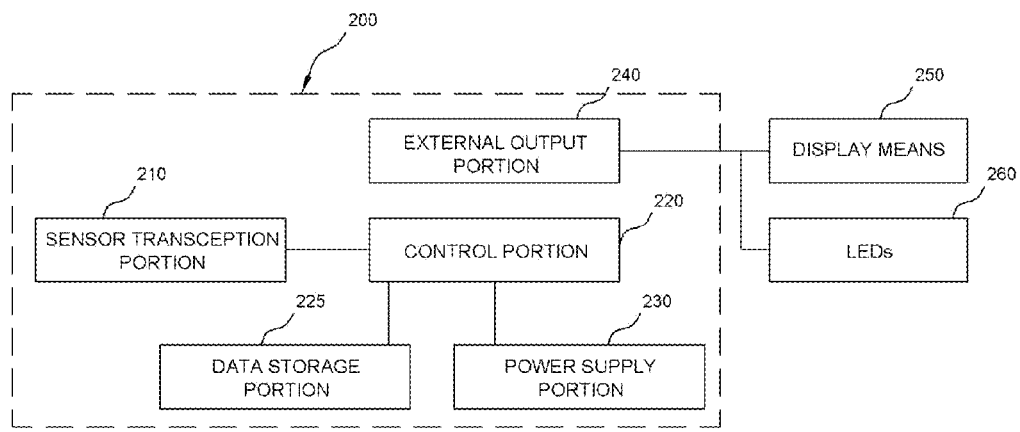
FIG. 8 is a block diagram illustrating an internal structure of a concentration meter according to one embodiment of the present invention.

As illustrated in FIG. 8, the concentration meter 200 includes, but not limited to, a sensor transception portion 210, a control portion, 220, a power supply portion 230, an external output portion 240, a display means 250, and LEDs 260. The sensor transception portion 210 amplifies an ultrasonic signal transmitted and received by the ultrasonic sensor portion 100 in order to enable high power transmission and high gain reception. The control portion 220 is mounted with a Process Condition Monitoring (PCM) algorithm so that the control portion 220 can implement a measurement mode suitable for on-site conditions, determine whether a process is normal or abnormal, and perform manipulation and control related to measurement of concentration. The power supply portion 230 supplies power needed by the control portion 220 and the sensor transception portion 210. The external output portion 240 outputs data of measurements of concentration measured by the control portion 220 to an external device. The display means 250 is connected to the external output portion 240 and offers a numeric display function, a process display function, and a diagnosis display function, a data trend display function. The LEDs 260 indicate states of various instruments.

That is, the concentration meter 200 is equipped with operation switches which are manipulated by a process manager for operation of equipment, setting of menu, and outputting of measurements. The concentration meter 200 has a signal amplification function which amplifies and filters the signal transmitted or received by the ultrasonic sensor portion 100, and a data logging function which stores data of the measurements as much as data of maximum 400 days in the storage portion 225.

The control portion is also mounted with an Envelope Energy Average Method (EEAM) algorithm to quantify the received signal, in addition to the PCM algorithm.

Figure 9:
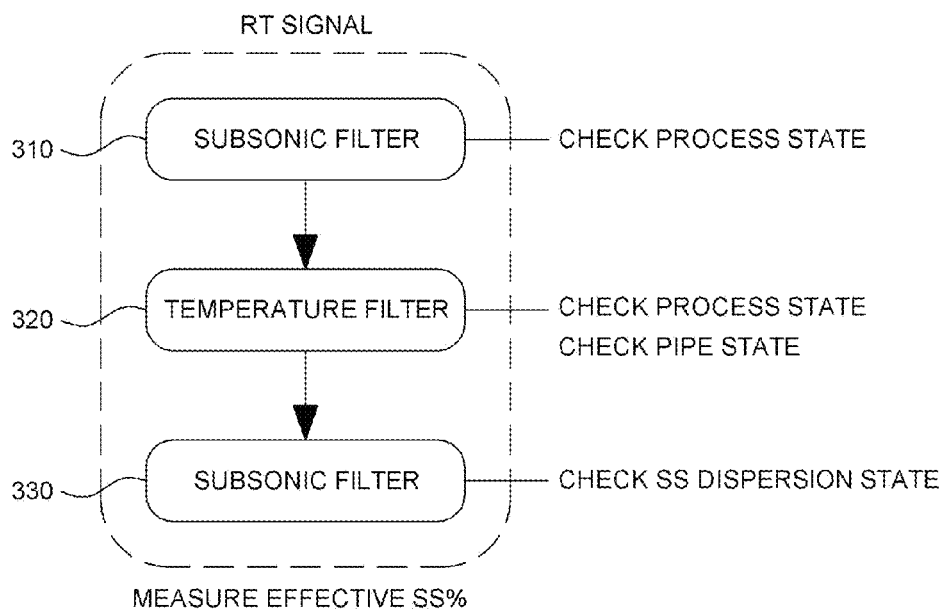
FIG. 9 is a schematic view describing the operation principle of a PCM algorithm according to one embodiment of the present invention.

With reference to FIG. 9, the PCM algorithm includes a subsonic filter 310 which measures a sound velocity through the fluid serving as a subject of measurement, and detects a change in the sound velocity, a temperature filter 320 which measures a temperature of the fluid serving as a subject of measurement and detects a change in the temperature of the fluid, and a signal filter 330 which receives a ultrasonic signal and detects an intensity of the ultrasonic signal or an amount of change in the ultrasonic signal.

The PCM algorithm checks a state of a process by means of the subsonic filter 310, a state of a process and a state of a pipe by means of the temperature filter 320, and a uniformity of dispersion of Suspended Solids (SS) which is a target of concentration measurement by means of the signal filter 330. After the checking is finished, the PCM algorithm determines an operation state (i.e. run or stop) of the process by collectively evaluating the results from the filters and determines the uniformity of dispersion of the SS, thereby provides a process operator with information such as a measured value of concentration of effective SS, a process operation state (i.e. run or stop), and a pipe filling state (i.e. full or empty).

The PCM algorithm verifies the values which are measured in real time by filtering the received ultrasonic signal and the temperature signal using the filters 310, 320, and 330, and selectively uses only the values which meet the standard. In this way, the PCM algorithm measures a concentration by reflecting the process operation state, thereby improving reliability and stability of products.

In addition, the PCM algorithm can perform concentration measurement in a Real Time (RT) mode in which changes in concentration are monitored in real time according to an on-site operation pattern and in a Process Monitoring (PM) mode in which changes in concentration are automatically monitored, only while a process is running, according to the result of the Process Control Monitoring (PCM).

Figure 10:
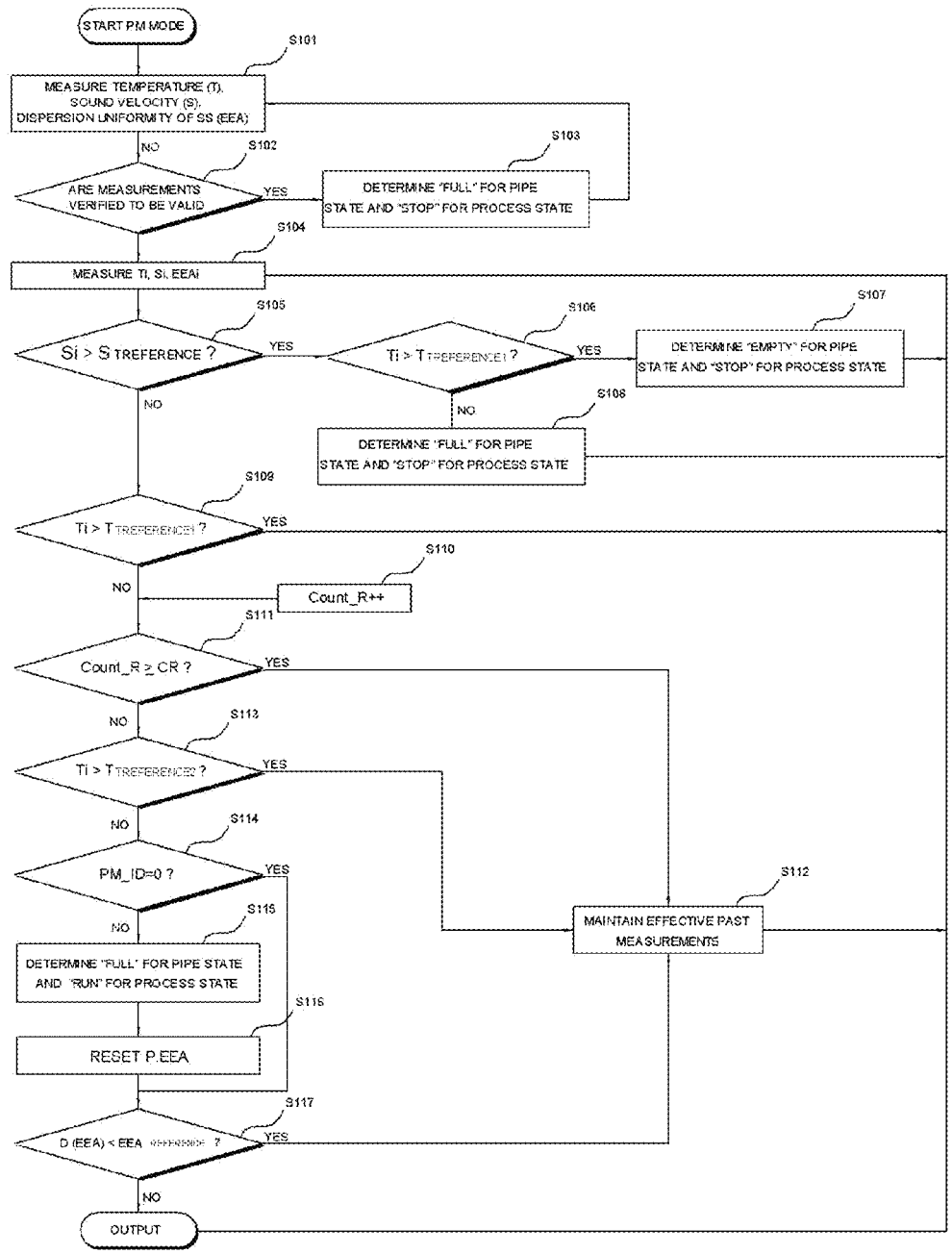
FIG. 10 is a flowchart illustrating a clamp-on-type ultrasonic concentration metering method according to one embodiment of the present invention.
Figure 11A:
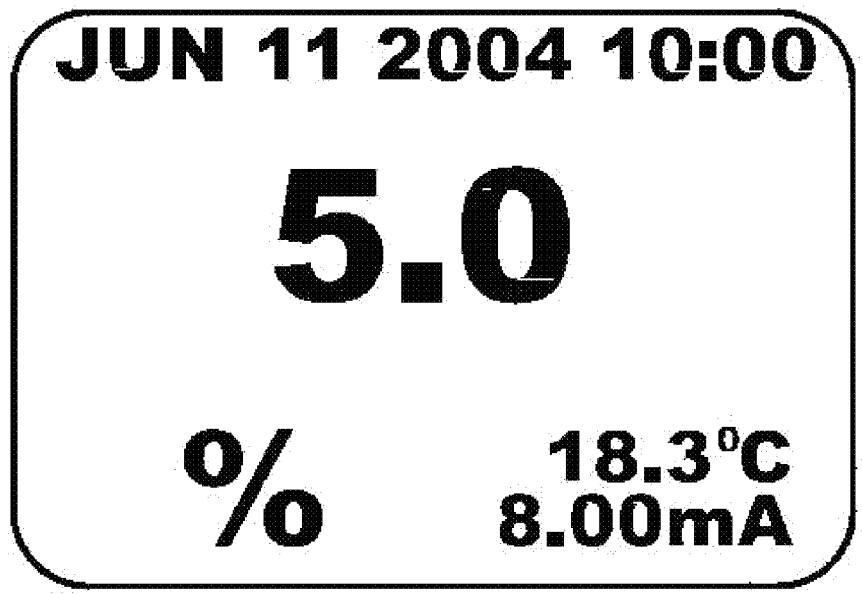
FIG. 11a is a view illustrating a display screen in which a numeric display is displayed according to one embodiment of the present invention.
Figure 11B:
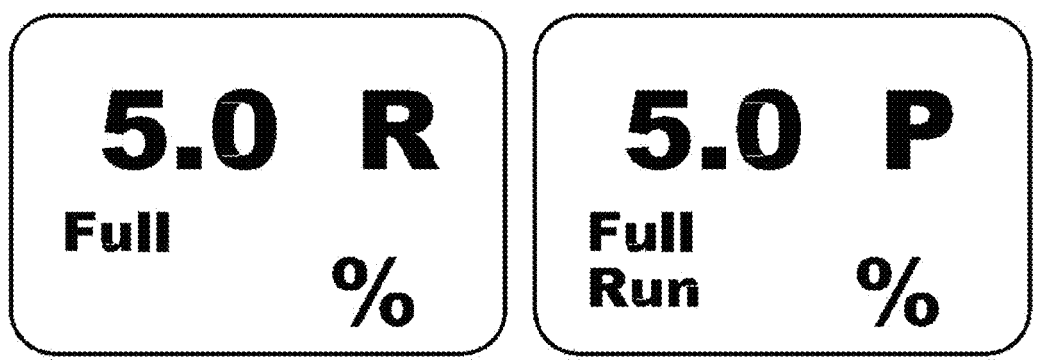
FIG. 11b is a view illustrating a display screen in which a process display is displayed according to one embodiment of the present invention.
Figure 11C:
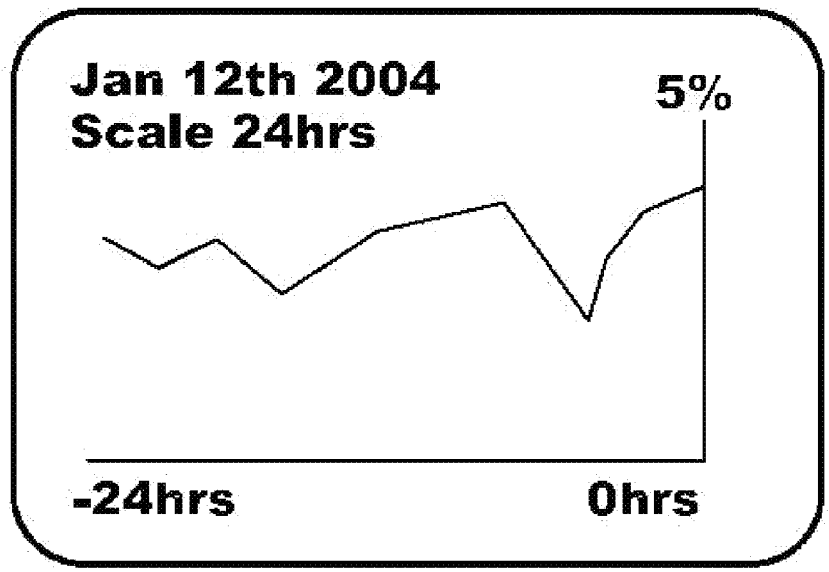
FIG. 11c is a view illustrating a display screen in which a data trend display is displayed according to one embodiment of the present invention.
Figure 11D:
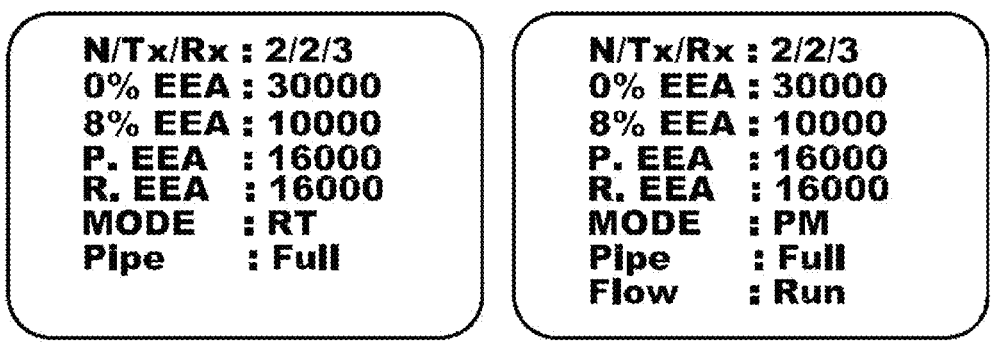
FIG. 11d is a view illustrating a display screen in which a diagnosis display is displayed according to one embodiment of the present invention.

As illustrated in FIG. 10, in the PM mode, the PCM algorithm measures the temperature and sound velocity of the fluid serving as a subject of measurement, and the dispersion uniformity EEA of suspended solids serving as a target of concentration measurement by means of the subsonic filter 310, the temperature filter 320, and the signal filter 330 (Step S101).

The ultrasonic signal received by the ultrasonic sensor portion 100 and the temperature signal are filtered to verify whether the values measured in real time are valid or not (Step S102). When the values are verified to be valid, the state is diagnosed as "empty" for the pipe filling state and "stop" for the process operation state (Step S103). When the values are verified to be invalid, a temperature Ti, a sound velocity Si, and a dispersion uniformity EEAi are measured (Step S104).

When the Si measured in Step S104 exceeds a reference sound velocity $S_{reference}$ and when the Ti exceeds a first reference temperature $T_{reference1}$, the state is diagnosed as "empty" for the pipe filling state and "stop" for the process operation state (Steps S105, S106, and S107).

On the other hand, when the Si measured in Step S104 exceeds the reference sound velocity $S_{reference}$ and when the Ti is the first reference temperature $T_{reference1}$ or below, the state is diagnosed as "full" for the pipe filling state and "stop" for the process operation state (Steps S105, S106, and S108). When the Si measured in Step S104 is equal to or lower than the reference sound velocity $S_{reference}$, and when the Ti is the first reference temperature $T_{reference1}$ or below, the number of times that the process operation state is diagnosed (hereinafter referred to as "process operation state diagnosis count") Count_R is counted up (Steps S109 and S110). When the process operation state diagnosis count Count_R is equal to or larger than a reference count CR, the measured values which have been verified to be valid are maintained (Steps S111 and S112).

When the process operation state diagnosis count Count_R is smaller than the reference count CR and when the measured real-time temperature Ti is above a second reference temperature $T_{reference2}$, the measured values which have been verified to be valid are maintained (Steps S113 and S112).

On the other hand, when the Ti is the second reference temperature $T_{reference2}$ or below, and when a PM state variable is not "0", the state is diagnosed as "full" and "run" and then the PM state variable is changed to "1" (Steps S114 and S115).

Next, the EEA value measured in the PM mode is reset. Next, when a difference d (EEA) between the measured EEA values is smaller than a reference EEA value, the measured past values which have been verified to be valid are maintained (Steps S116 and S117). Conversely, when the difference d (EEA) is equal to or larger than the reference EEA value, the PM mode is finished.

In this case, the $S_{reference}$ is a sound velocity frequency serving as a determination criterion to distinguish between the state "run" and the state "stop", and is automatically adjusted according to process operation patterns. The $T_{reference1}$ is a reference temperature to distinguish between "run" and "stop" for the process operation state and between "full" and "empty" for the pipe filling state. The $T_{reference2}$ is a reference temperature for choosing an effective EEA value. The $T_{reference1}$ and the $T_{reference2}$ are automatically adjusted according to process operation patterns.

The EEA reference value is a reference value used to prevent an excessive change in the EEA and uses a value obtained through experience. A PM_ID refers to a PM state variable (1 represents "run" and 0 represents "stop").

As illustrated in FIGS. 11a to 11d, the display means 250 has four visual screen modes including a numeric display mode, a process display mode, a diagnosis display mode, and a data trend display mode and performs a display using a graphic LCD for convenience of users.

In the numeric display mode, the display means displays basic information about measurements such as a present time, a concentration (SS), a unit of concentration (%), and output values of temperature and current. In the process display mode, the display means displays a value of a concentration (SS %) which is presently measured, and a present measurement mode. For representation of the present measurement mode, the RT mode is displayed as R, and the PM mode is displayed as P. In this mode, in addition, information about the process operation state, such as "run"

(representing "process being running") and "stop" (representing "process being stopped"), is also displayed. Furthermore, information about the pipe filling state, such as "full" representing "pipe being full" and "empty" representing "pipe being empty", is also displayed.

In the data trend display mode, the display means displays measured values (time and density of sludge) which are stored in the control portion 220 in the form of a graph on the spot. The values in the graph are values, which are represented with a certain data logging period, on a time axis and a concentration axis.

In the diagnosis display mode, the display means collectively displays the number of transmitted pulses, the intensity of a signal that the sensors can transmit and receive, the reference EEA value, the real-time and process EEA values, the measurement mode, the pipe filling state, and the process operation state.

Among the items of the information displayed in the diagnosis display mode, the intensity means the real-time intensity of a signal that the sensors 110 and 120 can transmit and receive (N represents the number of pulses, Tx represents the intensity of a signal transmitted, and Rx represents the intensity of a signal received); the reference EEA value represents a preset EEA value (0% represents 0% for the EEA value, 8% represents 8% or 20% for the EEA value, and R.EEA represents an EEA value in the real time mode); the measured EEA value represents a real-time EEA value for each measurement mode (P.EEA represents an EEA value in the process mode and R.EEA represents an EEA value in the real time mode); the measurement mode represents a mode in which the system is presently being operated (RT represents the real time mode and PM represents the process diagnosing mode); the pipe filling state means whether the inside of a pipe is full or empty ("full" represents that the pipe is full, and "empty" represents that the pipe is empty); and the process operation state means whether a process is running or stopped ("run" represents that the process is running, and "stop" represents that the process is stopped).

Hereinafter, the operation of the clamp-on-type ultrasonic concentration metering system according to one embodiment of the present invention is described in greater detail with reference to the drawings.

The clamp-on-type ultrasonic concentration metering system according to one embodiment of the present invention is improved in convenience of an operator and a user because the ultrasonic sensor portion 100 for measurement of concentration is attached to an outer wall of the pipe 50. Furthermore, the clamp-on-type ultrasonic concentration metering system can shield the ultrasonic sensor portion 100 from structural noise and has a lightweight design.

The concentration meter 200 includes the sensor transception portion 210, the control portion 220, the power supply portion 230, and the data storage portion 225 which are embodied as a hardware structure. The sensor transception portion 210 can amplify an ultrasonic signal to be transmitted and an ultrasonic signal received, can transmit a high power ultrasonic signal and receive a high-gain ultrasonic signal, and is capable of obtaining a high-gain, low-noise, amplified signal, using a hardware structure. The control portion 220 performs operation and control on measurement of concentration, control on transmission and reception of sensors, setting of menu types, setting of parameters, and logging of data of measurements.

The control portion 220 measures a concentration using an ultrasonic signal which is transmitted through a fluid serving as a subject of measurement, calculates an effective measurement value which is controllable by analyzing the concentration using a PCM algorithm, and outputs the effective measurement value to the external output portion 240.

That is, the control portion 220 performs amplification of a signal, verification of a signal, calculation of a concentration, and processing the measurement result into a certain form (i.e. analog form, digital form, or relay form) desired by a user.

The concentration meter 200 is mounted with a PCM algorithm which is a piece of software to determine whether a process operation state is normal or abnormal by executing an optimal measurement mode suited for the on-site operation pattern, thereby enabling reliable concentration measurement.

The PCM algorithm measures a concentration only when a process is running after determining whether the process is running or stopped and whether the pipe is full or empty, thereby enabling reliable concentration measurement needed in the field. Furthermore, the PCM algorithm determines whether the pipe 50 is empty or full and notifies an operator or a user of the result of the determination, thereby helping the operator or a user be aware of whether the process operation state is normal or abnormal.

In this way, by applying a PCM algorithm to an ultrasonic concentration metering system, it is possible to optimally measure a concentration according to a process operation pattern in the field, and to implement an optimum measurement mode suited for each type of water treatment plant, such as a plant which is periodically operated (i.e. a running period and a stop period are fixed every day), a plant which is operated around the clock, and a plant which is non-periodically operated (i.e. operated for a short period of time as necessary).

The PCM algorithm selects an optimum measurement mode from among the real time measurement mode (RT) and the process diagnosis operation mode (PM).

The ultrasonic sensor portion 100 uses PMNPT monocrystal to increase sensitivity, compared to a conventional insertion-type ultrasonic sensor, so that the ultrasonic sensor portion 100 has a sensitivity 4 to 5 times the sensitivity of a PZT used for a conventional ultrasonic sensor.

Furthermore, the ultrasonic sensor portion 100 can be attached to the pipe using a coupling structure of any one type selected from a handcuff type, a saddle type, and a clamp type which enables easy installation and easy shifting, so that a user can conveniently use the ultrasonic sensor portion 100. Moreover, the ultrasonic sensor portion 100 can perform reliable measurement without being affected by vibrations of surrounding pipes.

With environmental industry for water treatment growing in a market volume and environment improvement becoming a global issue, by developing an ultrasonic concentration metering system which is a key part for water treatment to reduce environmental pollution by wastewater and sewage, it is possible to accurately and precisely measure a concentration of sludge during treatment of water, thereby preventing excessive chemical treatment for sludge.

Furthermore, since it is possible to perform automatic control on concentration measurement according to operation patterns in the field, an amount of sludge generated during water treatment is reduced. As a result, energy saving is achieved because reduced sludge leads to a decrease in wasteful use of a pump for sludge treatment. Moreover, since it is possible to measure a total amount of pollutants through measurement of a concentration of the pollutants, a management system which reflects actual toxicity and harmfulness of pollutants in operation of a process can be constructed.

Although a preferred embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention relates to a clamp-on-type concentration metering system and method, and more particularly to a clamp-on-type concentration metering system and method for which a high sensitivity ultrasonic sensor portion is attached to an outer wall of a pipe, which can perform reliable concentration measurement according to fluctuations in fluid circulation conditions by determining a process operation state (run or stop) and a pipe filling state (full or empty), and which can be easily installed and maintained.

What is claimed is:

1. A clamp-on-type ultrasonic concentration metering system, comprising:
   an ultrasonic sensor portion that is attached to an outer wall of a pipe through which a fluid to be measured flows and that transmits and receives an ultrasonic signal through an wall of the pipe; and
   a concentration meter that measures a concentration of a substance according an intensity of the ultrasonic signal that is received after passing through the wall of the pipe, the fluid to be measured, and the wall of the pipe by means of the ultrasonic sensor portion and,
   wherein the ultrasonic sensor portion comprises:
      an ultrasonic transmission sensor that is attached to one-side wall of the pipe and transmits an ultrasonic signal which can pass through the fluid; and
      an ultrasonic reception sensor that is attached to the opposite-side wall of the pipe and receives the ultrasonic signal transmitted by the ultrasonic transmission sensor and,
   wherein the concentration meter comprises:
      an operation switch which is operated for process operation, setting of menu, and outputting of measurements during concentration measurement;
      a sensor transception portion that amplifies an ultrasonic signal transmitted or received by the ultrasonic sensor portion to enable high power transmission and high gain reception of the ultrasonic signal;
      a control portion mounted with a Process Condition Monitoring (PCM) algorithm, which performs an optimum concentration measurement mode for a field, determines whether a process operation state is normal or abnormal, and performs operation and control related to concentration measurement;
      a power supply portion that supplies power needed by the control portion and the sensor transception portion; and
      an external output portion that outputs measurements of concentration measured by the control portion.

2. The clamp-on-type ultrasonic concentration metering system according to claim 1, wherein each of the ultrasonic transmission sensor and the ultrasonic reception sensor comprises:
   a piezoelectric element that transmits or receives an ultrasonic signal; a sound-absorbing member that reduces residual vibrations of the ultrasonic transmission sensor or the ultrasonic reception sensor;
   an acoustic window that protects the piezoelectric element and maximizes ultrasonic signal transmission characteristics transmitted between media through impedance matching with the fluid to be measured;
   an external housing having a protective, waterproof, and noise-shielding structure that can protect the ultrasonic transmission sensor or the ultrasonic reception sensor from surrounding environments; and
   a connecter that is electrically connected to the concentration meter.

3. The clamp-on-type ultrasonic concentration metering system according to claim 1, wherein each of the ultrasonic transmission sensor and the ultrasonic reception sensor comprises a sensor that accommodates the corresponding sensor and an external casing that accommodates the sensor holder and is attached to the pipe.

4. The clamp-on-type ultrasonic concentration metering system according to claim 3, wherein the external casing is any one type selected from the group consisting of a handcuff type which fixedly installs the sensor, a clamp type by which fixedly installs the sensor, and a saddle type which movably installs the sensor.

5. The clamp-on-type ultrasonic concentration metering system according to claim 3, wherein the external casing uses a casing guide which aligns the external casing with respect to the pipe when the external casing is designed originally.

6. The clamp-on-type ultrasonic concentration metering system according to claim 3, wherein the sensor holder is pivotably supported to the external casing, and the sensor is rotatable, so that an angle of the sensor with respect to the pipe is adjustable according to a shape of a radiating surface of the sensor.

7. The clamp-on-type ultrasonic concentration metering system according to claim 1, wherein the external output portion is connected to a display means and provides a numeric display function, a process display function, a diagnosis display function, and a data trend display function.

8. The clamp-on-type ultrasonic concentration metering system according to claim 1, wherein the PCM algorithm comprises:
   a subsonic filter that measures a sound velocity of the fluid to be measured and determines a change in the sound velocity;
   a temperature sensor that measures a temperature of the fluid to be measured and determines a change in the temperature; and;
   a signal filter that receives the ultrasonic signal and determines an intensity of the ultrasonic signal and an amount of change in the intensity of the ultrasonic signal.

9. The clamp-on-type ultrasonic concentration metering system according to claim 8, wherein the PCM algorithm checks a process state using the subsonic filter, the process state and a pipe filling state using the temperature filter, and a dispersion uniformity of suspended solids that are targets of concentration measurement using the signal filter, determines a process operation state by collating results from each filter, determines the dispersion uniformity of the suspended solids, and provides a process operator with information about measurements of effective suspended solids, the process operation state, and the pipe filling state during operation of a process.

10. The clamp-on-type ultrasonic concentration metering system according to claim 1, wherein the PCM algorithm mode has measurement modes including a real time mode in which a change in concentration is monitored in real time according to an on-site operation pattern and a process monitoring mode in which a change in concentration is automatically measured only while a process is running, based on a result of a process condition monitoring (PCM).

* * * * *